US006852342B2

(12) United States Patent (10) Patent No.: US 6,852,342 B2
Teague et al. (45) Date of Patent: Feb. 8, 2005

(54) COMPOUNDS FOR ALTERING FOOD INTAKE IN HUMANS

(75) Inventors: Richard King Teague, Edenton, NC (US); Samuel Leonard Tynch, Edenton, NC (US); Frank Louis Jaksch, Jr., Irvine, CA (US); Richard Theodore Maier, Jr., Hertford, NC (US)

(73) Assignees: Avoca, Inc., Merryhill, NC (US); ChromaDex, Inc., Santa Ana, CA (US)

( * ) Notice: Subject to any disclaimer, the term of this patent is extended or adjusted under 35 U.S.C. 154(b) by 0 days.

(21) Appl. No.: 10/108,036

(22) Filed: Mar. 26, 2002

(65) Prior Publication Data

US 2003/0185919 A1 Oct. 2, 2003

(51) Int. Cl.$^7$ .................................................. A61K 35/78
(52) U.S. Cl. ........................ 424/725; 424/757; 514/909
(58) Field of Search ................................. 424/725, 757; 514/909

(56) References Cited

U.S. PATENT DOCUMENTS

| | | | |
|---|---|---|---|
| 4,442,113 A | 4/1984 | Lassen et al. ............... | 424/267 |
| 4,897,390 A | 1/1990 | Ruhe ......................... | 514/177 |
| 5,612,039 A | 3/1997 | Policappelli et al. .... | 424/195.1 |
| 5,672,371 A | 9/1997 | d—Oosterlynck | |
| 5,904,923 A | 5/1999 | Morazzoni et al. ...... | 424/195.1 |
| 5,962,043 A | 10/1999 | Jones et al. | |
| 6,007,823 A | 12/1999 | Abbott et al. ............ | 424/195.1 |
| 6,113,949 A | 9/2000 | Brink ......................... | 424/602 |
| 6,207,638 B1 | 3/2001 | Portman ....................... | 614/2 |
| 6,224,873 B1 | 5/2001 | Jones ....................... | 424/195.1 |
| 6,238,672 B1 | 5/2001 | Chen ....................... | 424/195.1 |
| 6,245,364 B1 | 6/2001 | Jones et al. .................... | 426/2 |
| 6,277,396 B1 | 8/2001 | Dente ......................... | 424/439 |

FOREIGN PATENT DOCUMENTS

| NL | 8901639 | * 1/1991 |
|---|---|---|
| WO | WO 94/25035 | * 11/1994 |
| WO | WO 00/72861 | * 12/2000 |

OTHER PUBLICATIONS

McGraw, L. Agricultural Research. Dec. 2000. vol. 48, No. 12, pp. 21. PROMT Abstract enclosed.*
Arnouts, S., et al. "Jojoba meal (*Simmondsia chinensis*) in the Diet of Broiler Breeder Pullets: Physiological and Endocrinological Effects." *Poultry Science* 72:1714–1721 (1993).
Booth, Albert N., et al. "Isolation of a Toxic Factor from Jojoba Meal." *Life Sciences* 15(6):1115–1120 (1974).
Cokelaere, M., et al. "Reproductive Performance of Rats Treated with Defatted Jojoba Meal or Simmondsin Before or During Gestation." *Food and Chemical Toxicology* 36:13–19 (1998).

Cokelaere, Marnix M., et al. "Food Intake Inhibitory Activity of Simmondsin and Defatted Jojoba Meal: Dose–Response Curves in Rats." *Progress in New Crops* Ed. Jules Janick. Alexandria, VA: ASHS Press p. 377–382 (1996).
Cokelaere, M. M., et al. "Devazepide reverses the anorexic effect of simmondsin in the rat." *Journal of Endocrinology* 147:473–477 (1995).
Cokelaere, Marnix, et al. "Evidences for a satiating effect of defatted jojoba meal." *Industrial Crops and Products* 4:91–96 (1995).
Cokelaere, M., et al. "Influence of Long–Term Simmondsin Administration on Thyroid Hormone Levels in Adult Rats." *Hormone and Metabolic Research* 27:318–321 (1995).
Cokelaere, Marnix M., et al. "Fertility in Rats after Long–Term Jojoba Meal Supplementation." *Journal of Agricultural and Food Chemistry* 41:1449–1451 (1993).
Cokelaere, Marnix M., et al. "Influence of Jojoba Meal Supplementation on Growth and Organ Funciton in Rats." *Journal of Agricultural and Food Chemistry* 41:1444–1448 (1993).
Cokelaere, Marnix M., et al. "Influence of Pure Simmondsin on the Food Intake in Rats." *Journal of Agricultural and Food Chemistry* 40:1839–1842 (1992).
Cokelaere, Marnix M., et al. "Investigation of Possible Toxicological Influences of Simmondsin after Subacute Administration in the Rat." *Journal of Agricultural and Food Chemistry* 40:2443–2445 (1992).
Elliger, C.A., A.C. Waiss, Jr. & R.E. Lundin "Cyanomethylenecyclohexyl Glucosides from *Simmondsia californica.*" *Phytochemical Reports* 13:2319–2320 (1974).
Elliger, Carl A., Anthony C. Waiss, Jr. & Robert E. Lundin "Simmondsin, an Unusual 2–Cyanomethylenecyclohexyl Glucoside from *Simmondsia californica.*" *Journal of the Chemical Society Perkin Transactions 1* 2209–2212 (1973).
"Final Report on the Safety Assessment of Jojoba Oil and Jojoba Wax." *Journal of the American College of Toxicology* 11(1):57–74 (1992).
Flo, G., et al. "The vagus nerve in involved in the anorexigenic effect of simmondsin in the rat." *Appetite* 34:147–151 (2000).
Flo, Gerda, et al. "Absorption and Excretion of Simmondsin after Different Administration Routes in Rats." *Journal of Agricultural and Food Chemistry* 45:185–188 (1997).

(List continued on next page.)

*Primary Examiner*—Christopher R. Tate
(74) *Attorney, Agent, or Firm*—Hoffman & Baron, LLP

(57) ABSTRACT

The present invention relates to a process of providing an extract containing at least one simmondsin compound. The extract is provided from jojoba plant, and used as a dietary supplement for use in a weight control regiment in humans. The present invention also provides a method of treating an overweight human in need of such treatment, and comprises administering a therapeutically effective amount of such an extract.

14 Claims, No Drawings

OTHER PUBLICATIONS

Frank, Richard L. & Tish Eggleston Pahl "Nutraceuticals—food, Dietary Supplement, or Drug?" *Biotechnology Law Report* 18(2):131–143 (1999).

"Investigation of the physiological actions and pharmacology of Simmondsin as anorexigenic glucoside from the jojoba plant." *Laboratory of Toxicology and Food Chemistry* Online Available http://www.farm.kuleuven.ac.be/toxico/english/simmondsin.htm May 4, 2001.

Manos, Charles G., et al. "Toxicologic Studies with Lambs Fed Jojoba Meal Supplemented Rations." *Journal of Agricultural and Food Chemistry* 34:801–805 (1986).

McGraw, Linda "ARS Researchers Develop New Markets for Jojoba." *Agricultural Research Service News Service* Dec. 5, 2000. Online. Internet. May 4, 2001.

Medina, Luis A. & Augusto Trejo–Gonzalez "Detoxified and Debittered Jojoba Meal: Biological Evaluation and Physical–Chemical Characterization" *Cereal Chemistry* 67(5):476–479 (1990).

Ngou, Jean Daniel, et al. "Evaluation of Jojoba Meals for Rabbits and Poultry." *Federation Proceedings* 41(3):354 (1982).

Storlie, Jean, et al. "Food or Supplement? Choosing the Appropriate Regulatory path." *Food Technology* 52(12):62–68 Dec. 1998.

Van Boven, M., et al. "Extraction and liquid chromatographic method for the determination of simmondsin in plasma." *Journal of Chromatography B* 665:281–285 (1994).

Verbiscar, Anthony J., et al. "Detoxification of Jojoba Meal by Lactobacilli." *Journal of Agricultural and Food Chemistry* 29:296–302 (1981).

Verbiscar, Anthony J., et al. "Detoxification of Jojoba Meal." *Journal of Agricultural and Food Chemistry* 28:571–578 (1980).

Wallace, Phil. "FDA to allow dietary supplement claims failing to meet its 'gold standard' proof." *Dietary Supplement & Food Labeling News* 9(1):1+ Oct. 11, 2000.

Wantke, F., et al. "Contact dermatitis from jojoba oil and myristyl lactate/maleated soybean oil." *Contact Dermatitis* 34(1):71–72 (1996).

Weber, Charles W. & B.L. Reid "Toxic Effects of Simmondsin in Growing and Reproducing Mice." *Federation Proceedings* 34(3):226 (1975).

Elliger, C. A. et al., J. Chem. Soc. Perkin Trans., I2209–2212 (1973).

Elliger, C. A. et al., Phytochemistry 13, pp. 2319–2320 (1974).

Manos, C. G. et al., J. Agric. Food Chem. 34, pp. 801–805 (1986).

Flo, G et al., Appetite, 34, pp. 147–151 (2000).

Cokelaere, M. et al., Food Chem. Toxicol., 36, pp. 13–19 (1998).

Cokelaere, M. et al., Ind. Crops Prod., 4, pp. 91–96 (1995).

Cokelaere, M. et al., Horm. Metab. Res. 27, pp. 318–321 (1995).

Cokelaere, M. et al., J. Agric. Food Chem. 41, pp. 1449–1451 (1993).

Cokelaere, M. et al., J. Agric. Food Chem. 40, pp. 2443–2445 (1992).

Cokelaere, M. et al., J. Agric. Food Chem. 40, pp. 1839–1842 (1992).

Cokelaere, M. et al., J. Agric. Food Chem. 41, pp. 1444–1448 (1993).

Booth, A. N. et al., Life Sciences, 15 (6), pp. 1115–1120 (1974).

Verbiscar, A. J. et al., J. Agric. Food Chem., 28, pp. 571–578 (1980).

Arnouts, S. et al., Poultry Science 72, pp. 1714–1721 (1993).

Medina, L. A. et al., Cereal Chem. 67 (5), pp. 476–479 (1990).

Verbiscar, A. J. et al., J. Agric. Food Chem., 29, pp. 296–302 (1981).

Van Boven, M. et al., J. Chromatography B, 655, pp. 281–285 (1994).

J. Am. Coll. Toxicol., 11 (1), Ch. 5, pp. 57–74 (1992).

* cited by examiner

COMPOUNDS FOR ALTERING FOOD INTAKE IN HUMANS

FIELD OF THE INVENTION

The present relates to materials derived from jojoba plants that are useful for promoting good health and feeling of well-being, and particularly for altering food intake in humans, and more particularly to materials useful for suppressing appetite, and in human weight control programs.

BACKGROUND OF THE INVENTION

With respect to humans and appetite suppression or weight control, a wide variety of low-calorie foods, dietary supplements, pharmaceuticals, medical foods, functional foods and nutraceutical agents have been suggested. Additionally, a number of dietary weight loss and weight control programs have been suggested, many of which incorporate the use of dietary supplements or therapeutic agents. Known therapeutic agents (e.g., as drugs) and known dietary supplements act by a variety of mechanisms. Exemplary drugs include epinephrine (as a pure substance, or in the form within the ephedra herb), norepinephrine, 5-hydroxytryptamine (e.g., flenfluramine), phenylpropanolamine, phentermine, and various amphetamines. The active agents within those drugs have been demonstrated to have some degree of efficacy, but are subject to disadvantages. For example, phenteramine has potential side-effects like nervousness, insomnia, and constipation. Moreover, patients generally develop a tolerance to the drug, and certain programs lasting longer than about eight weeks often are not desirable or feasible. Fenfluramine has been associated with primary pulmonary hypertension (PPH), a deadly disorder in which the blood vessels of the lungs are destroyed. There also has been an interest in investigating dietary supplements and active ingredients that are derived from natural sources. See, for example, U.S. Pat. No. 6,224,873 to Jones.

A natural material that has been associated with altering appetite in animals is derived from portions of the jojoba plant. The jojoba plant, *Simmondsia californica* or *S. chinenese*, is an evergreen shrub that grows wild in Arizona, lower California, and western Mexico. Recently jojoba has been grown, planted, and cultivated as a domestic crop. Typically, the jojoba plant is cultivated for its seeds from which a wax ester oil is removed. The resultant oil is used in cosmetic formulations and lubricant formulations. Portions of the jojoba plant also are used as a feedstock for livestock. See, for example, Elliger et al., *J. Chem. Soc. Perkin Trans.* I 2209–2212 (1973).

Jojoba meal has a high content of simmondsin compounds, and in particular, simmondsin (I), simmondsin-2'-ferulate (II), and related cyanomethylenecyclohexyl glycosides (Elliger et al., *Phytochemistry* 13, 2319 (1974) and Manos et al., *J. Agric. Food Chem.* 34, 801–805 (1986)). Simmondsin compounds have been demonstrated to alter appetite in rats (Flo et al., *Appetite*, 34 147–151 (2000), Cokelaere et al., *Food Chem. Toxicol.* 36, 13–19 (1998), Cokelaere et al., *Ind. Crops Prod*, 4 91–96 (1995), Cokelaere et al., *Horm. Metab. Res.*, 318–321 (1995), Cokelaere et al., *J. Agric. Food Chem.* 41, 1449–1451 (1993), Cokelaere et al., *J. Agric. Food Chem.* 40, 2443–2445 (1992), Cokelaere et al., *J. Agric. Food Chem.* 40, 1839–1842 (1992), Cokelaere et al., *J. Agric. Food Chem.* 41, 1444–1448 (1993), and Booth et al., *Life Sciences* 15(6), 1115–1120 (1974)); mice (Verbiscar et al., *J. Agric. Food Chem.* 28, 571–578 (1980)); chickens (Arnouts et al., *Poultry Science* 72, 1714–1721 (1993); and domestic cats and dogs (U.S. Pat. No. 6,245,364 to Jones et al and U.S. Pat. No. 5,962,043 to Jones et al).

Various techniques for separating simmondsins compounds from jojoba meal have been suggested. See, for example, Medina et al., *Cereal Chem.* 67(5) 476–479 (1990), Verbiscar et al., *J. Agric. Food Chem.* 29, 296–302 (1981), Verbiscar et al., *J. Agric. Food Chem.* 28, 571–578 (1980) and Booth et al., *Life Sciences* 15(6), 1115–1120 (1974). Furthermore, U.S. Pat. No. 6,007,823 to Abbott et al. proposes a method for isolation of simmondsin compounds. Typically, simmondsin compounds are first extracted from defatted jojoba meal using water. After separation, the water extract is isolated and water removed to provide the simmondsin compounds as a solid extract. Individual simmondsin compounds are isolated from the dried extract by contact with a first ethanolic solvent forming a first solvent fraction. The first solvent fraction is then separated from the solid phase and the ethanolic solvent removed by drying. See, also, U.S. Pat. No. 5,672,371 to d'Oosterlynck.

It would be desirable to provide a composition derived from a natural source (e.g., a jojoba extract containing at least one simmondsin compound), in a form to be administered as a beneficial or therapeutic composition for the purpose of controlling the intake of food in humans. Such controlled intake of food can be used as part of a treatment program for various eating disorders and related conditions (e.g., obesity).

SUMMARY OF THE INVENTION

In one embodiment, the present invention provides a process of extracting components incorporating at least one simmondsin compound from a jojoba plant (or portion of jojoba plant). The process comprises contacting a portion of jojoba plant (e.g., jojoba meal) with an organic solvent to provide a mixture. The portion of jojoba meal and organic solvent mixture is heated, preferably while mixing or otherwise agitating that mixture. The resulting solvent containing extracted components of the jojoba plant is separated from that portion of the jojoba plant that is insoluble in the solvent. The resulting mixture of extract and solvent is concentrated, such as by applying further heat, and preferably by subjecting that mixture to reduced pressure relative to atmospheric pressure, to provide a mixture comprising at least one extracted simmondsin compound. The mixture can be mixed with other components (e.g., starch-type carriers) and dried. For example, the mixture can be spray dried to provide a powder. The resulting powder then can be formulated into a desirable form (and optionally with other suitable components) for ingestion or administration, such as a capsule or tablet.

Jojoba extracts containing at least one extracted simmondsin compound can be used in a convenient form to be administered to, or ingested by, a human patient or subject for the purpose of altering the desire for intake of food and beverage, and for associated weight control. That is, those jojoba extracts can be ingested or administered to a human in order to modify eating habits, and hence control his/her intake of food. Those jojoba extracts also can also be used as a means to satiate hunger or as an appetite suppressant. As such, ingestion or administration of those jojoba extracts acts as a way to control the weight of a human (e.g., by decreasing a subject's desire for food and by promoting good eating habits, thus resulting in weight loss). Jojoba extracts incorporating at least one extracted simmondsin compound can be used to supplement a diet (e.g., as a dietary supplement), wherein a portion of food intake is supplemented or replaced by the ingestion of at that jojoba extract. Such a jojoba extract can be part of a specific regiment under the administration and control of a medical doctor. Such an extract preferably is taken at predetermined times during a day, and in predetermined amounts; occasionally (e.g., on a day-by-day basis), or regularly over a period or periods of time (e.g., as part of a dietary program). In one embodiment, a therapeutically effective amount of at least one simmondsin compound can be taken at least once a day, preferably prior to a meal. In an alternate embodiment, at least one simmondsin compound is taken before (e.g., at least one hour prior to commencement of) any or each of the three meals that a human would eat in a normal daily routine. Proper and effective use of jojoba extracts containing at least one simmondsin compound can result in significant weight loss, assist in weight control, or assist in maintaining good eating habits for subjects that might otherwise have poor or unhealthy eating habits. Proper and effective use of those jojoba extracts also can result in those subjects having the feeling of being more energetic, and of having improved physical performance.

DETAILED DESCRIPTION OF THE INVENTION

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

As summarized above, the present invention relates to a process of extracting components incorporating at least one simmondsin compound from a portion of the jojoba plant to provide a composition obtained from a natural source and suitable for controlling the intake of food and beverage. Such control of the intake of food can be used to modify eating behavior and to treat various eating disorders. Ingestion of a beneficial amount of a jojoba extract containing an effective amount of at least one natural simmondsin compound can be used to curb or suppress appetite, promote a healthy diet or healthy eating habits, or reduce craving for food. For example, a major characteristic of obesity is overeating. Control of behavior associated with overeating can act to reduce the total number of calories ingested, and as a result, an effective weight loss program can be developed. Similarly, bulimia is characterized by patients, typically females, having an inability to become satiated by food but avoiding weight gain by regurgitating recently ingested food. Thus, the jojoba extract may be used to satiate hunger in such patients, and the resulting undesirable symptoms associated with that disorder can be reduced, minimized or eliminated.

A dietary supplement is defined under the Dietary Supplement Health and Education Act of 1994 ("DSHEA"). A dietary supplement is a product (other than tobacco) intended to supplement the diet, and contains one or more of the following dietary ingredients: a vitamin; a mineral; an herb or other botanical; an amino acid; a dietary substance for use by a human to supplement the diet by increasing the total dietary intake; or a concentrate, metabolite, constituent, extract, or combination of any of those ingredients. The product is intended for ingestion in tablet, capsule, powder, softgel, gelcap, or liquid form. As defined by DSHEA, a dietary supplement is not represented for use as a conventional food or as a sole item of a meal or of the diet.

As used herein and in the claims, the terms "beneficially effective amount" or "therapeutically effective amount" mean an amount of material or composition sufficient to significantly induce a positive modification in the condition to be treated, but low enough to avoid serious side effects (at a reasonable benefit/risk ratio) within the scope of sound medical judgment. The beneficially or therapeutically effective amount of the material or composition can vary depending upon factors such as the particular condition being treated, the overall metabolism of the person, the age and physical condition of the person, the severity of the condition, the overall metabolism of that person, the duration of the treatment, the nature of concurrent therapy, the specific composition employed, the desire of the person to have improved eating habits, and like factors within the knowledge and expertise of the medical community.

Jojoba extracts, jojoba extracts containing simmondsin compounds and simmondsin compounds can be provided using a variety of known techniques. Various techniques for separating the simmondsin compounds from jojoba meal have been suggested. See, for example, Medina et al., *Cereal Chem.* 67(5) 476–479 (1990), Verbiscar et al., *J. Agric. Food Chem.* 29, 296–302 (1981), Verbiscar et al., *J. Agric. Food Chem.* 28, 571–578 (1980) and Booth et al., *Life Sciences* 15(6), 1115–1120 (1974). See, also, U.S. Pat. No. 6,007,823 to Abbott et al. and U.S. Pat. No. 5,672,371 to d'Oosterlynck, the disclosures of which are incorporated herein by reference in their entireties. However, simmondsin compounds also can be provided from jojoba plant using the process steps and conditions of the present invention.

The starting point for providing a jojoba extract containing a relatively high content of at least one simmondsin compound involves contacting the jojoba plant, or a portion of the jojoba plant with an organic solvent. The jojoba plant can be in a form that has not been previously subjected to extraction with any type of solvent, such as with an aqueous solvent. The jojoba plant or portion thereof also can be used in a form wherein the jojoba plant in its natural form has undergone some type of physical or chemical processing. For example, a portion of jojoba plant preferably is used in the form of jojoba meal. Jojoba meal typically is the residue left after oils are removed from the seeds of the jojoba plant. A preferred form of jojoba meal is defatted jojoba meal. Sources of jojoba meal and the manner of preparation of jojoba meal will be readily apparent to those skilled in the art of jojoba plant harvesting and processing. The jojoba plant also can be pre-treated with agents capable of enhancing the effectiveness of extraction of simmondsin compounds therefrom.

The jojoba plant is contacted with an organic solvent to provide a mixture. The organic solvent is used to extract relevant components from within the jojoba plant. Those components can be extracted from the jojoba plant using a solvent that is in the form of a liquid, or the components can be extracted using a suitable solvent under supercritical extraction conditions or supercritical-type conditions. The organic solvent can be anhydrous or non-anhydrous in nature. Suitable organic solvents include compounds containing at least one carbon atom, and include alkanes (e.g., pentanes, heptanes, hexanes, octanes and cyclohexane), alcohols (e.g., methanol, ethanol, propanols, butanols, pentanols and other types of lower alcohols), ethers (e.g, diethyl ether), petroleum ethers, halocarbons and halogenated hydrocarbons (e.g., dichloromethane), carbonyl-containing compounds (e.g., acetone and methyl ethyl ketone), and other organic compounds, such as toluene and ethyl acetate. Solvents typically used for the extraction in the food and dietary supplement industries are particularly preferred, and food grade solvents are of particular interest. For example, food grade denatured ethanol is a particularly preferred solvent. For purposes of the present invention, an organic solvent is a liquid solvent comprised primarily of organic liquid, or a supercritical fluid comprising at least one compound containing at least one carbon atom, and can be essentially pure organic solvent. Supercritical fluids can include carbon dioxide, compound such as the alkanes (e.g., including methane, ethane, butane and pentane), halocarbons, halogenated hydrocarbons, on combinations thereof. Supercritcal fluid and supercritical-type extraction materials, equipment, procedures and conditions suitable for extracting components of plant materials are well known. See, for example, U.S. Pat. No. 4,153,063 to Roselius; U.S. Pat. No. 4,506,682 to Muller; U.S. Pat. No. 4,714,617 to Gahrs; U.S. Pat. No. 5,018,540 to Grubbs et al.; U.S. Pat. No. 5,435,325 to Clapp et al.; U.S. Pat. No. 5,554,382 to Castor; U.S. Pat. No. 5,639,431 to Castor and U.S. Pat. No. 6,095,134 to Sievers et al.; U.S. Pat. No. 6,111,108 to Lopez-Avila and U.S. Pat. No. 6,291,241 to Castor et al.; the disclosures of which are incorporated herein by reference in their entireties.

In one aspect of the present invention, the jojoba plant or portion thereof is extracted by contacting that plant with a co-solvent mixture, such as a mixture of two or more organic solvents, or a mixture of an alcohol and a liquid having an aqueous character. A preferred co-solvent mixture is a mixture composed primarily of organic solvent and some liquid having an aqueous character (e.g., wherein the organic an aqueous solvents are highly dispersible in one another). One suitable alcohol is ethanol, and one suitable liquid having an aqueous character can be water in the form of tap water, distilled water, or the like. For example, for purposes of the present invention, the organic solvent can be considered to be a co-solvent mixture, and such a mixture can contain about 70 percent to about 95 percent ethanol, and about 5 percent to about 30 percent water, on a weight basis. The solvent or co-solvent mixture can include pH buffers, pH adjusters, organic and inorganic salts, sugars, surfactants, agents to facilitate extraction, or other additives.

The conditions under which the extraction is performed can vary. Extractions using liquid organic solvents typically are carried out under conditions of atmospheric pressure, or under slight vacuum conditions (e.g., about 3 to about 10 inches of water column vacuum). Conditions of temperature can be less than, greater than, or equal to, ambient temperature. Typical temperatures (depending upon the characteristics of the solvent or co-solvent mixture) can range from about 5° C. to about 125° C., often about 10° C. to about 90° C., and frequently about 15° C. to about 85° C. It is most preferred that the extraction be carried out while the mixture of jojoba plant and solvent is maintained at temperatures above ambient temperature. As such, preferred extraction conditions involve heating that mixture. The heating is often performed at a temperature of about 5° C. to about 25° C. less than the boiling point of the solvent in the jojoba plant/solvent mixture. For example, when an ethanol/water co-solvent mixture is used, extraction of the jojoba plant is carried out at a temperature from about 20° C. to about 80° C., preferably about 50° C. to about 70° C. The extraction also can be carried out under the supercritical conditions of the organic solvent (i.e., under conditions of temperature and pressure that define supercritical conditions or supercritical-type conditions).

The extraction preferably is performed at an optimized solvent to jojoba plant ratio, namely at a ratio wherein a relatively large amount of extract is extracted from the jojoba plant using a balance of the optimum and minimum amount of solvent. Typically, the lower amount of solvent used, the more concentrated the extract within the solvent. The ratio of organic solvent to jojoba meal for the extraction preferably is about 3:1 to about 10:1, and often is about 4:1 to about 6:1, on a weight basis.

The manner by which the extraction is carried out can vary. The extraction can be carried out using a liquid organic solvent in a batch or continuous manner. Suitable equipment used to carry out the extraction will be readily apparent to those skilled in the art of extraction of natural materials, such as vegetables, fruits, herbs, and the like. Exemplary extraction equipment is commercially available and is used throughout the food and dietary supplement industries. Exemplary types of extraction equipment can include high shear blenders, food processing mills, counter current extractors, mixing drums, percolators, static mixers, and the like. Preferred extraction equipment is suitably equipped to provide the desired heating of the mixture being extracted. For example, extractors can be equipped with suitable heating jackets. Preferably, the mixture that is being subjected to extraction conditions is agitated. That is, the mixture of solvent and jojoba plant experiences some type of movement during the extraction period, and that movement is supplied in order to facilitate extraction of the desired components from the jojoba plant by the solvent. Such agitation can be provided by high shear mixing, stirring, squeezing, shaking, or other like types of movement. Suitable extraction techniques and apparatus are described in U.S. Pat. No. 5,234,008 to Fagg and U.S. Pat. No. 5,360,022 to Newton, the disclosures of which are incorporated herein by reference in their entireties.

The solvent and extracted components therein are separated from the insoluble portion of the jojoba plant. As such, jojoba "pulp" is separated from the liquid portion of the processed mixture. It is desirable to remove as much of the dispersed and insoluble portions from the mixture as possible, however, it is not strictly necessary to remove virtually all of the dispersed and insoluble portions from the solvent containing the extracted components. Techniques for such separation will be readily apparent to those having skill in the art of slurry handling, and in liquid extraction of vegetables, fruits, herbs and other plant materials. Suitable techniques involve the use of filters, screens, centrifuges, presses, screw presses, rotating disk presses, converging belts, and the like. As such, significantly high amounts of the desired jojoba plant extract and solvent are obtained, and isolated.

The resulting mixture of solvent and jojoba plant (or solvent and processed jojoba plant portion) then is concentrated. Preferably, the concentration step is carried out promptly after the mixture incorporating liquid organic solvent has been heated, in order that the mixture being concentrated still retains the heat supplied by the previous heating step. In the preferred embodiment, the mixture is concentrated by applying further heat to the mixture and subjecting the mixture to reduced pressure conditions (e.g., a vacuum) relative to ambient conditions to provide an extract comprising extracted at least one simmondsin compound. As such, when the solvent is a co-solvent mixture of ethanol and water, significant amounts the organic solvent and water are removed from the mixture. When reduced pressure conditions are employed, typical temperatures at which the concentration is carried out can range from about 30° C. to about 90° C., normally about 40° C. to about 70° C. Reduced pressure conditions typically involve subjecting the mixture to distillation conditions under vacuum of about 15 to about 28 inches water column. The resulting concentrated mixture containing extracted simmondsin compounds and other components extracted from the jojoba plant material preferably is from about 45 to about 75 percent solids, and often about 55 to about 65 percent solids. Solids are defined as components extracted from the jojoba plant, and those solids typically are dissolved or highly dispersed within that solvent. Of those solids, it is typical that about 5 to about 40 percent thereof, often about 10 to about 25 percent thereof, and more often about 10 to about 20 percent thereof, on a weight basis based on the total weight of the solids, is composed of one or more simmondsin compounds, which can include simmondsin(I) and simmondsin-related compounds, such as simmondsin-2'-ferulate(II) and other related cyanomethylenecyclohexyl glycosides.

The resulting concentrated mixture has further amounts of solvent removed therefrom. That is, extracted components can be further dried to the form of a solid, such as a powder. Suitable drying techniques will be readily apparent to those skilled in the art of the processing of natural materials. Exemplary drying techniques involve oven drying, tray drying, fluidized bed drying, drum drying, freeze drying and spray drying techniques, and the selection and operation of equipment associated with those drying techniques will be readily apparent to those skilled in the art of handling and processing foods and dietary supplements. Typically, dried material, such as spray dried material, exhibits a solvent content of less than about 10 percent, preferably less than about 5 percent, based on the total weight of that material. However, it is highly preferred that during drying essentially all of the solvent be removed from the concentrated extract mixture.

The process of the present invention allows for the efficient and effective preparation of jojoba extracts, and for obtaining simmondsin compounds from a natural source in an efficient and effective manner. High quality jojoba extracts can be obtained at high yield in an economical manner, using a high output process.

Dried extracts can be used as such, and can be ingested by, or administered to, humans in essentially neat form. However, those extracts can be combined with other suitable components or ingredients. In one regard, prior to drying, certain components (e.g., diluents or carriers, such as starches or modified starches) can be incorporated into the mixture of jojoba plant extract and solvent. For example, the mixture can be combined with components that are soluble or dispersible within the solvent of that mixture, or the mixture can be combined with components that result in the formation of a slurry. The mixture also can contain additives such as ingredients that assist in facilitation of the drying of the extract. For example, small amounts of silicon dioxide or other similar agents, such as Sipernet, can be incorporated as a powder during a spray drying process in order to assist in improving the flowability of the mixture. Alternatively, chilonsate powders of low bulk density can be used to increase the overall bulk density of a dried, powdered extract.

The jojoba extract, such as that extract described hereinbefore, is useful as a dietary supplement, a component of a functional food, a food additive, a medical food, or as a therapeutic agent. As such, the jojoba extract may be further formulated for administration in a pharmaceutical carrier, in either solid or liquid form, in accordance with known techniques. See, for example, Remington, *The Science And Practice of Pharmacy* ($9^{th}$ Ed. 1995). Examples of suitable carriers include, but are not limited to, starches, modified starches, gum arabic, calcium silicate, microcrystalline cellulose, methacrylates, shellac, polyvinylpyrrolidone, cellulose, water, syrup, and methylcellulose. Preferred carriers are compatible with other ingredients of the formulation, and do not result in deleterious side effects to humans who ingest the formulation. Carriers offer a convenient way to provide for a pre-determined and identifiable unit-dose type of formulation. Typically, use of carriers is such that at least about 10 weight percent of the formulation is provided by the simmondsin compounds of the jojoba extract. Therapeutic formulations also can include lubricating agents such as, for example, talc, magnesium stearate and mineral oil; wetting agents; emulsifying and suspending agents; preserving agents such as methyl- and propyl hydroxybenzoates; sweetening agents; or flavoring agents. Polyols, buffers, and inert fillers may also be used. Examples of polyols include, but are not limited to, mannitol, sorbitol, xylitol, sucrose, maltose, glucose, lactose, dextrose, and the like. Suitable buffers encompass, but are not limited to, phosphate, citrate, tartarate, succinate, and the like. Other inert fillers that may be used encompass those which are known in the art and are useful in the manufacture of various dosage forms. If desired, the solid formulations may include other components such as bulking agents and/or granulating agents, and the like. Therapeutic formulations contain the desired jojoba extracts that are suitably formulated so as to provide the desired quick, sustained, or delayed release of the active ingredient after administration to a patient in need thereof.

The formulations of the present invention can be administered in a variety of ways. Preferably, the formulations are ingested or otherwise orally administered. Alternatively, the formulations can be administered rectally, buccally (e.g., sub-lingually), parenterally (e.g., subcutaneously, intramuscularly, intradermally, or intravenously), or by other suitable means.

Formulations suitable for oral administration may be presented in discrete units, such as capsules, cachets, lozenges, or tablets, each containing a predetermined amount of the jojoba meal extract; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the jojoba extract and a suitable carrier (which may contain one or more accessory ingredients as noted above). In general, the formulations of the invention are prepared by uniformly and intimately admixing the jojoba extract with a liquid or finely divided solid carrier, or both, and then, if necessary, shaping the resulting mixture. For example, a tablet may be prepared by compressing or molding a powder or granules containing the jojoba extract, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder. As such, simmondsin compounds of a jojoba extract can be conveniently self-administered by the human ingesting those compounds. Preferred tablets or capsules containing jojoba extract and ingredients such as carriers typically contain about 10 to about 20 percent of active simmondsin compound, based on the total weight of such tablet or capsule.

Formulations suitable for buccal (sub-lingual) administration include lozenges comprising the jojoba extract in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the jojoba extract, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

Formulations suitable for rectal administration are preferably presented as unit dose suppositories. These may be prepared by admixing the jojoba extract with one or more conventional solid carriers, for example, cocoa butter, and then shaping the resulting mixture.

Most preferably, the jojoba extract containing an effective amount of at least one simmondsin compound is ingested orally and swallowed. Such a jojoba extract also may be consumed directly as a powder, as a tablet, or within a carrier made up of water, juice, tea, tisane, or the like. Alternatively, such a jojoba extract can be incorporated into solid food products or specialty food products.

Jojoba extracts containing simmondsin compound can be used as dietary supplements, and when used daily in a beneficial amount by a human, can create a feeling of satiation that can result in a reduction of that human's caloric intake. When used in the form of dietary supplements, jojoba extracts can ingested in the form of capsules, softgels or tablets. The jojoba extract can be formed into a capsule, typically of 0-size (e.g., about 500 mg) or 00-size (e.g., about 1000 mg). Such capsules typically are manufactured using ingredients, techniques and equipment commonly used for the manufacture of capsules for use within the dietary supplement industry. As an example, 3 capsules each containing 1000 mg of jojoba extract containing about 12 weight percent simmondsin compounds ingested daily by a 90 kg individual can provide a daily ingestion of about 4 mg simmondsin compounds per kilogram of that individual.

The jojoba extract also may be admixed with other ingredients to form the basis of a dietary product, which may either be a nutritional drink, or as a nutritional bar. The extract can be dispersed in water or juice, to create a drink that can be ingested in cold or warmed form. For example, simmondsin compounds can be included as part of a drink such as "Eclipse Deluxe Lipodize" available from Eclipse Sports Supplements, which is a combination of simmondsins from jojoba, phosphates, ashwagandha, guggul (gum) extract, capsaicin, and ginger extract. Another example is a nutritional bar that can provide about 15 grams of protein, about 26 grams of carbohydrate and about 5 grams of fat, in addition to a quantity of other ingredients, such as jojoba extract. Such products may thus be used as meal replacements by those seeking to lose weight, or by those requiring nutritional support during sporting activities, whereby the benefits of the extract are supported by the nutritional content of the food or beverage product.

The jojoba extract also may be given in combination with herbs that possess beneficial effects for humans, and particularly in respect to weight loss or improvements in physical performance. In this connection, suitable herbs and foods include those herbs and foods that contain methylxanthines such as caffeine, theobromine and theophylline. The simmondsin compounds can be used or administered in combination with appropriate counseling, a controlled diet, a low-calorie diet, and/or an exercise regime.

The beneficial or therapeutically effective dosage of any jojoba extract will vary somewhat depending upon each individual, and will depend upon factors such as the age and condition of the individual, the reasons behind the eating disorder that the individual may have, the reasons why the individual may be overweight, the frequency and manner of ingestion or administration of that extract, and other like factors. Such dosages can be determined in accordance with routine pharmacological procedures known to those skilled in the art. The beneficial amount typically will be dependent upon factors such as the weight of the individual, the eating habits of that individual, the reasons associated with that individual's habits of overeating, the metabolism of that individual, the type of food and beverage that individual n normally may ingest, and other such factors. See, Van Boven et al., *J. Chomatography B* 655, 281–285 (1994) and *J. Am. Coll. Toxicol.*, 11(1) Ch. 5 57–74 (1992).

The jojoba extract can be used in a wide variety of beneficial and therapeutic methods. For example, in one embodiment, the intake of food can be controlled by administering to a human, a beneficial amount of jojoba extract containing at least one simmondsin compound at least once a day prior to a meal for a pre-determined or specific time period (e.g., for a time period of about one week, two weeks, one month, or more). Alternatively, jojoba extract containing at least one simmondsin compound can be ingested or administered, either periodically or on a pre-determined and regimented basis, over an indefinite period of time. Such extracts also can be ingested or administered on a periodic basis, such as at one day intervals, and not a part of a regimented or daily program.

The amount of simmondsin compound within jojoba extract that ingested by, or administered to, a human on a daily basis can vary. The amount of simmondsin compound ingested or administered on a daily basis (i.e., over a 24 hour period) by a human can be at least about 2 mg, typically can be at least about 5 mg, often can be at least about 10 mg, frequently can be at least about 15 mg, and even can be at least about 20 mg, of total simmondsin compound per kilogram of that human. If taken in smaller, multiple dosages (e.g., two or three times per day), the amount of simmondsin compound ingested or administered on a daily basis (i.e., over a 24 hour period) by a human can be at least about 15 mg, typically can be at least about 25 mg, often can be at least about 35 mg, even can be at least about 45 mg, of total simmondsin compound per kilogram of that human. Typically, the amount of simmondsin compound ingested or administered on a daily basis (i.e., over a 24 hour period) by a human does not exceed about 200 mg, usually does not exceed 150 mg, often does not exceed about 100 mg, and frequently does not exceed about 75 mg, of total simmondsin compound per kilogram of that human. Typically, a 24 hour period is a calendar day. Although the amount jojoba extract ingested or administered can vary from person to person, and from day to day, the foregoing amounts of jojoba extract can be essentially safe and can provide a beneficial effect.

The time period over which a human uses the jojoba extract to control overeating, or to promote good eating habits, can vary. The time period can vary from occasional use at one-day or two-day intervals, to a long term program whereby the jojoba extract is ingested or administered on an essentially daily basis for an indefinite period of time. In one regard, jojoba extract can be administered on an essentially daily basis as part of a program aimed at reducing the weight of a human be a predetermined amount, or to a desired weight. For example, such a program can be described as a method for reducing the weight of a human by administering a beneficially effective amount of a jojoba extract at least once a day until the human patient has reduced his/her weight (as determined immediately prior to the program) by at least 10 percent, or even by at least 20 percent.

The time of day that the jojoba extract is ingested or administered can vary. The jojoba extract can be taken once a day, or at several intervals throughout the day. The time of day that jojoba extract is ingested or administered can depend upon the individual human, and his/her normal eating habits. For example, jojoba extract can be ingested or administered early in the day, in order that a feeling of satiation is provided during morning hours; or later in the day, in order that a feeling of satiation is provided during evening hours. Alternatively, jojoba extract can be ingested or administered during time periods between normal mealtimes, in order to control the intake of food and beverage between meals, in activities known as "snacking." In one embodiment, a beneficial or therapeutic amount of a suitable jojoba extract is provided to a human patient prior to a meal (e.g., at least about 30 minutes, and preferably at least about one hour, prior to a meal). As used herein, the term "meal" has the normal meaning of a pre-determined menu of food ingestion at a pre-determined time. Normally, a healthy human eats at least one meal known as breakfast, lunch or dinner in a 24 hour period and in particular during a calendar day. Thus, for example, it is possible to ingest or administer jojoba extract in early morning hours prior to breakfast, in late morning hours prior to lunch, and in early evening hours prior to dinner.

The feeling of satiation provided by ingestion or administration of simmondsin compounds derived from jojoba extract provides for a reduction in the amount food or beverage ingested by a human, as measured by food volume, food weight or caloric intake. The feeling of satiation results in a decreased intake of food, either at meals, or as a result of food intake between meals by eating activities known as snacking. Components of jojoba extracts, and in particular simmondsin compounds, act to suppress appetite and provide less craving for food, thus causing subjects to eat less and hence lose weight.

Depending upon the amount of jojoba extract ingested, and the time or times of day that the composition is ingested, an individual human's daily caloric intake can be reduced, relative to the normal average caloric intake that individual may experience. For individuals weighing in excess of 75 kilograms, ingestion of beneficial amounts of simmondsin compound derived from jojoba extract can reduce average daily caloric intake to due consumption of food and beverage by more than 100 calories per day, and even more than 200 calories per day. For individuals weighing in excess of 100 kilograms, ingestion of beneficial amounts of simmondsin compound derived from jojoba extract can reduce average daily caloric intake to due consumption of food and beverage by more than 100 calories per day, often more than 200 calories per day, and even more than 500 calories per day.

The following examples are provided in order to further illustrate various embodiments of the invention and are not to be construed as limiting the scope thereof.

EXAMPLE 1

Jojoba meal purchased as de-fatted jojoba meal from American Mercantile Corporation) is extracted using ethanol and water at a ratio of 80 percent ethanol and 20 percent water, on a weight to weight basis. In particular, about 6 liters of the ethanol/water mix and about 1 kilogram of the jojoba meal are added to a slurry extractor. The resulting mixture is heated to 60° C., and held at that temperature for one hour while mixing is continued. The resulting mixture is filtered through a centrifuge, and the centrifuge cake is washed with an ethanol/water mix until the dissolved solids leaving the centrifuge is less than 1 weight percent. The resulting liquid comprising water, ethanol and the dissolved solids of the jojoba meal is concentrated by heating to 50° C. under reduced pressure (relative to atmospheric pressure) of 27 inches of water column vacuum, using a distillation unit. As a result, there is obtained a water, ethanol and extract mixture (supernatant) having a concentration of 65 percent solids, on a weight basis. The concentration of simmondsin compounds within the extract portion of the mixture is about 20 percent, based on the weight of the extract portion of the mixture. For a desired final product in powdered form and having an overall simmondsin compound concentration of 12 weight percent (as determined by high performance liquid chromatography), a slurry is prepared from 6 grams of the aforementioned mixture and 4 grams of a modified food starch (i.e., Capsul™ from National Starch Company). The resulting slurry of mixture and modified food starch then is dried using an atomizer wheel spray dryer set at an inlet temperature of 200° C. and an outlet temperature of 100° C., to provide a naturally-derived composition in powdered form.

EXAMPLE 2

Jojoba extract is provided as described in Example 1. The resulting powder, which contains about 12 weight percent of simmondsin compounds(as determined by high performance liquid chromatography), is formed into capsules of approximately 250 mg in weight. The capsules were ingested by 16 human subjects. Those subjects ingested between 2 and 5, usually 3 or 4, of those capsules throughout (normally from 1 to 3 times) a 24 hour day. Of those subjects, 11 reported weight loss. Those subjects reporting positive results reported weight loss, appetite suppression and an increase in energy. Some subjects reported having diarrhea.

The foregoing is illustrative of the present invention, and is not to be construed as limiting thereof. Accordingly, the invention is defined by the following claims, with equivalents of the claims to be included therein.

That which is claimed:

1. A method for controlling the intake of food in a human, the method comprises administering to the human a beneficially effective amount of a composition containing at least one simmondsin compound extracted from at least a portion of a jojoba plant, wherein said amount is sufficient to cause control of intake of food by the human, and wherein administration occurs about thirty minutes prior to a meal.

2. The method according to claim 1, whereby the simmondsin compound is administered in an amount of at least 2 mg per kilogram of human.

3. The method according to claim 1, whereby the administration occurs three times per 24 hour period.

4. The method according to claim 1, whereby administration occurs about 3 times per day for at least one week.

5. A method for modifying the eating habits of a human, the method comprises administering to the human a beneficially effective amount of a composition containing at least one simmondsin compound extracted from at least a portion of a jojoba plant, wherein said amount is sufficient to cause control of intake of food by the human, and wherein said administration occurs about thirty minutes prior to a meal.

6. The method according to claim 5, whereby the simmondsin compound is administered in an amount of at least 2 mg per kilogram of human.

7. The method according to claim 5, whereby the administration occurs three times per 24 hour period.

8. The method according to claim 5, whereby the administration occurs about 3 times per 24 hour period for at least a one week period.

9. A method for controlling weight of a human, the method comprises administering to the human a beneficially effective amount of a composition containing at least one simmondsin compound extracted from at least a portion of a jojoba plant, wherein said amount is sufficient to cause control of intake of food by the human, and wherein said administration occurs about thirty minutes prior to a meal.

10. The method according to claim 9, whereby the simmondsin is administered in an amount of at least 2 mg per kilogram of human.

11. The method according to claim 9, whereby the administration occurs three times per 24 hour period.

12. The method according to claim 9, whereby the administration occurs about 3 times per 24 hour period for at least a 1 week period.

13. The method according to claim 9, whereby the simmondsin compound is administered in an amount of at least 5 mg per kilogram of human.

14. The method according to claim 9, whereby the simmondsin compound is administered in an amount of at least 10 mg per kilogram of human.

* * * * *